US012618857B2

(12) United States Patent (10) Patent No.: US 12,618,857 B2
Goldman et al. (45) Date of Patent: **\*May 5, 2026**

(54) METHODS FOR DETECTING ESTRONE BY MASS SPECTROMETRY

(71) Applicant: Quest Diagnostics Investments Incorporated, Wilmington, DE (US)

(72) Inventors: Mildred M. Goldman, Laguna Niguel, CA (US); Richard E. Reitz, San Clemente, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 931 days.

This patent is subject to a terminal disclaimer.

(21) Appl. No.: 17/700,258

(22) Filed: Mar. 21, 2022

(65) Prior Publication Data

US 2022/0214364 A1 Jul. 7, 2022

Related U.S. Application Data

(63) Continuation of application No. 16/579,438, filed on Sep. 23, 2019, now Pat. No. 11,280,798, which is a
(Continued)

(51) Int. Cl.
*G01N 33/74* (2006.01)
*G01N 33/68* (2006.01)

(52) U.S. Cl.
CPC ....... *G01N 33/743* (2013.01); *G01N 33/6851* (2013.01); *G01N 2560/00* (2013.01);
(Continued)

(58) Field of Classification Search
CPC ............. G01N 33/743; G01N 33/6851; G01N 2560/00; G01N 27/62; G01N 27/628;
(Continued)

(56) References Cited

U.S. PATENT DOCUMENTS 5,772,874 A 6/1998 Quinn et al.
5,795,469 A 8/1998 Quinn et al.
(Continued)

FOREIGN PATENT DOCUMENTS

JP 2001116736 A 4/2001
JP 2003090839 A 3/2003
(Continued)

OTHER PUBLICATIONS

Nelson et al., Liquid Chromatography-Tandem Mass Spectrometry Assay for Simultaneous Measurement of Estradiol and Estrone in Human Plasma, Feb. 1, 2004, Clinical Chemistry, vol. 50, Issue 2, pp. 373-384 (Year: 2004).*
(Continued)

*Primary Examiner* — Benjamin R Whatley
*Assistant Examiner* — Curtis A Thompson
(74) *Attorney, Agent, or Firm* — Quest Diagnostics, Inc.

(57) ABSTRACT

Provided are methods for determining the amount of estrone in a sample using mass spectrometry. The methods generally involve ionizing estrone in a sample and detecting and quantifying the amount of the ion to determine the amount of estrone in the sample.

8 Claims, 1 Drawing Sheet

Linearity – Typical Calibration Curve

E 1

Y = 0.0782019+0.00136918*X+9.78803e-008*X^2
R^2 = 0.9996  W: Equal

Related U.S. Application Data continuation of application No. 15/616,657, filed on Jun. 7, 2017, now Pat. No. 10,422,804, which is a continuation of application No. 14/533,602, filed on Nov. 5, 2014, now Pat. No. 9,678,087, which is a continuation of application No. 12/002,314, filed on Dec. 13, 2007, now Pat. No. 8,916,385.

(52) U.S. Cl.
CPC .... *Y10T 436/20* (2015.01); *Y10T 436/200833* (2015.01); *Y10T 436/203332* (2015.01); *Y10T 436/24* (2015.01); *Y10T 436/25* (2015.01)

(58) Field of Classification Search
CPC .. G01N 27/64; G01N 27/68; G01N 2333/575; Y10T 436/20; Y10T 436/200833; Y10T 436/203332; Y10T 436/24; Y10T 436/25
See application file for complete search history.

(56) References Cited

U.S. PATENT DOCUMENTS

| | | | |
|---|---|---|---|
| 5,919,368 A | 7/1999 | Quinn et al. | |
| 5,968,367 A | 10/1999 | Quinn et al. | |
| 6,107,623 A | 8/2000 | Bateman et al. | |
| 6,124,137 A | 9/2000 | Hutchens et al. | |
| 6,204,500 B1 | 3/2001 | Whitehouse et al. | |
| 6,268,144 B1 | 7/2001 | Koester | |
| 7,473,560 B2 | 1/2009 | Soldin | |
| 7,618,827 B2 | 11/2009 | Soldin | |
| 8,916,385 B2 | 12/2014 | Goldman et al. | |
| 9,678,087 B2 * | 6/2017 | Goldman | G01N 33/743 |
| 10,422,804 B2 * | 9/2019 | Goldman | G01N 33/6851 |
| 11,280,798 B2 * | 3/2022 | Goldman | G01N 33/6851 |
| 2003/0092601 A1 | 5/2003 | Polansky | |
| 2006/0040256 A1 | 2/2006 | Caulfield et al. | |
| 2006/0105408 A1 | 5/2006 | Hazen et al. | |
| 2007/0043441 A1 | 2/2007 | Pisharodi | |
| 2008/0128606 A1 * | 6/2008 | Grant | G01N 33/743 250/288 |

FOREIGN PATENT DOCUMENTS

| | | |
|---|---|---|
| JP | 2005283380 A | 10/2005 |
| WO | 2006107339 A2 | 10/2006 |
| WO | 2007044153 A1 | 4/2007 |
| WO | 2007092873 A2 | 8/2007 |
| WO | 2007139956 A2 | 12/2007 |

OTHER PUBLICATIONS

Anari et al., Derivatization of Ethinylestradiol with Dansyl Chloride to Enhance Electrospray Ionization: Application in Trace Analysis of Ethinylestradiol in Rhesus Monkey Plasma, Aug. 15, 2002, Analytical Chemistry, vol. 74, pp. 4136-4144 (Year: 2002).*

Xu et al., A liquid chromatography-mass spectrometry method for the quantitative analysis of urinary edogenous estrogen metabolites, May 24, 2007, Nature Protocols, vol. 2, No. 6, pp. 1350-1355 (Year: 2007).*

Koh et al., Determination of steroid estrogens in wastewater by high performance liquid chromatography-tandem mass spectrometry, Oct. 10, 2007, Journal of Chromatography, 1173, pp. 81-87 (Year: 2007).*

Xia et al., Trace level quantification of deuterated 17β-estradiol and estrone in ovariectomized mouse plasma and brain using liquid chromatography/tandem mass spectrometry following dansylation reaction, Apr. 9, 2004, Rapid Communications in Mass Spectrometry, vol. 18, Issue 14, pp. 1621-1628 (Year: 2004).*

Bouchonnet et al., Elucidation of the dissociation pathways of electro-ionized estrone, Jan. 2010, Rapid Communications in Mass Spectrometry, Wiley InterScience, 24: 973-978 (Year: 2010).*

Borges et al., Characterisation of estrone-nucleic acid adducts formed by reaction of 3,4-estrone-o-quinone with 2'-deoxynucleosides/deoxynucleotides using capillary liquid chromatography/electrospray ionization mass spectrometry, Jul. 2004, Rapid Communications in Mass Spectrometry, 18, 2191-2200 (Year: 2004).*

Dig et al., Derivatization procedures for the detection of estrogenic chemicals by gas chromatography/mass spectrometry, Aug. 2002, Rapid Communications in Mass Spectrometry, 17, 56-63) disclose derivatization procedures for detecting estrone by mass spectrometry. (Year: 2002).*

Xu et al., 1,2-Dimethylimidazole-4-sulfonyl chloride, a novel derivatization reagent for the analysis of phenolic compounds by liquid chromatography electrospray tandem mass spectrometry: Application to 1-hydroxypyrene in human urine, May 2007, Journal of Chromatography B, 855, pp. 159-165. (Year: 2007).*

Bouchonnet et al., Elucidation of the dissociation pathways of electro-ionized estrone, Jan. 2010, Rapid Communications in Mass Specrometry, Wiley InterScience, 24: 973-978 (Year: 2010).*

Yan Q., et al., "Determination of Anabolic Hormones Multi-residues in Animal Muscle Tissues Using Liquich Chromatography-Tandem Mass Spectrometry," Chinese Journal of Analytical Chemistry, 2006, vol. 34 (3), pp. 298-302.

Zimmer D., et al., "Comparison of Turbulent-Flow Chromatography with Automated Solid-Phase Extraction in 96-Well Plates and Liquid-Liquid Extraction Used as Plasma Sample Preparation Techniques for Liquid Chromatography-Tandem Mass Spectrometry," Journal of Chromatography A, 1999, vol. 854, pp. 23-35.

Adlercreutz G., et al., "Mass Fragmentographic Determination of Eleven Estrogens in the Body Fluids of Pregnant and Nonpregnant Subjects," Journal of Steroid Biochemistry, 1974, vol. 5, pp. 211-217.

Bartolucci G., et al., "Liquid Chromatography Tandem Mass Spectrometric Quantitation of Sulfamethazine and its Metabolites: Direct Analysis of Swine Urine by Triple Quadrupole and by Ion Trap Mass Spectrometry," Rapid Communications in Mass Spectrometry, 2000, vol. 14 (11), pp. 967-973.

De-Alda M.J.L., et al., "Review of Analytical Methods for the Determination of Estrogens and Progestogens in Waste Waters," Fresenius Journal of Analytical Chemistry, 2001, vol. 371, pp. 437-447.

Diaz-Cruz M.S., et al., "Determination of Estrogens and Progestogens by Mass Spectrometric Techniques (GC/MS, LC/MS and LC/MS/MS)," Journal of Mass Spectrometry , 2003, vol. 38 (9), pp. 917-923.

Dorgan A.F., et al., "Measurement of Steroid Sex Hormones in Serum: A Comparison of Radioimmunoassay and Mass Spectrometry," Steroids, 2002, vol. 67 (3-4), pp. 151-158.

European Search Report for Application No. 17203354.0 mailed on Mar. 1, 2018, 12 pages.

Extended European Search Report for Application No. 08859581.4, mailed on Feb. 25, 2011.

Extended European Search Report for Application No. 14176286.4, mailed on Oct. 8, 2014, 10 pages.

Extended European Search Report for Application No. 20191596.4, mailed on Oct. 26, 2020.

Extended European Search Report for Application No. EP18176001, mailed on Jul. 4, 2018, 9 pages.

Final Office Action mailed Oct. 12, 2010 for U.S. Appl. No. 12/002,314, filed Dec. 13, 2007.

Final Office Action mailed Jul. 21, 2011 for U.S. Appl. No. 12/002,314, filed Dec. 13, 2007.

Guasch-Jane M.R., et al., "Liquid Chromatography with Mass Spectrometry in Tandem Mode Applied for the Identification of Wine Markers in Residues from Ancient Egyptian Vessels," Analytical Chemistry, 2004, vol. 76 (6), pp. 1672-1677.

Guo T., et al., "Steroid Profiles Using Liquid Chromatography-Tandem Mass Spectrometry with Atmospheric Pressure Photoionization Source," Archives of Pathology & Laboratory Medicine, 2004, vol. 128 (4), pp. 469-475.

Higashi T., et al., "Procedure for Increasing the Detection Responses of Estrogens in LC-MS Based on Introduction of a Nitrobenzene

(56) References Cited

OTHER PUBLICATIONS

Moiety Followed by Electron Capture Atmospheric Pressure Chemical Ionization," Analytical and Bioanalytical Chemistry, 2006, vol. 386 (3), pp. 658-665.

Hobe G., et al., "Some New Aspects of 17alpha-Estradiol Metabolism in Man," Steroids, 2002, vol. 67 (11), pp. 883-893.

Hsu J.F., et al., "Evaluation of Electrospray Ionization and Atmospheric Pressure Chemical Ionization for Simultaneous Detection of Estrone and Its Metabolites using High-Performance Liquid Chromatography/Tandem Mass Spectrometry," Journal of Chromatography B, Elsevier, 2007, vol. 860 (1), pp. 49-56.

Inoue K., et al., "Application of Liquid Chromatography-Mass Spectrometry to the Quantification of Bisphenol A in Human Semen," Journal of Chromatography B, 2002, vol. 773 (2), pp. 97-102.

International Search Report for Application No. PCT/US2008/085282, mailed on Feb. 9, 2009, 2 Pages.

Lagana A., et al., "Trace Analysis of Estrogenic Chemicals in Sewage Effluent Using Liquid Chromatography Combined With Tandem Mass Spectrometry," Rapid Communications in Mass Spectrometry, 2000, vol. 14 (6), pp. 401-407.

Le-Bail J.C., et al., "Conversion of Dehydroepiandrosterone Sulfate at Physiological Plasma Concentration into Estrogens in MCF-7 Cells," Steroids, 2002, vol. 67 (13-14), pp. 1057-1064.

Lin D.L., et al., "Chemical Derivatization and the Selection of Deuterated Internal Standard for Quantitative Determination-methamphetamine Example." Journal of Analytical Toxicology, 2000, vol. 24 (4), pp. 275-280.

Lopez De-Alda M.J., et al., "Liquid Chromatography-(Tandem) Mass Spectrometry of Selected Emerging Pollutants (Steroid Sex Hormones, Drugs and Alkylphenolic Surfactants) in the Aquatic Environment," Journal of Chromatography B, 2003, vol. 1000 (1-2), pp. 503-526.

Merchant M., et al., "Recent Advancements in Surface-Enhanced Laser Desorption/Ionization-Time of Flight-Mass Spectrometry," Electrophoresis, 2000, vol. 21 (6), pp. 1164-1167.

Michael S.E., "The Isolation of Albumin from Blood Serum or Plasma by Means of Organic Solvents," Biochemical Journal, 1962, vol. 82 (1), pp. 212-218.

Nachtigall L.E., et al., "Serum Estradiol-Binding Profiles in Postmenopausal Women Undergoing Three Common Estrogen Replacement Therapies: Associations with Sex Hormone-Binding globulin, Estradiol, and Estrone Levels," Menopause, 2000, vol. 7 (4), pp. 243-250.

Nelson R.E., et al., "Liquid Chromatography-Tandem Mass Spectrometry Assay for Simultaneous Measurement of Estradiol and Estrone in Human Plasma," Clinical Chemistry, 2004, vol. 50 (2), pp. 373-384.

Nelson R.E., et al., "Measurement of Serum Estradiol and Estrone by LC-MS/MS," Clinical Chemistry, 2002, vol. 48 (6), pp. A132.

Non-Final Office Action mailed Jan. 2, 2019 for U.S. Appl. No. 15/616,657, filed Jun. 7, 2017.

Non-Final Office Action mailed Jan. 6, 2011 for U.S. Appl. No. 12/002,314, filed Dec. 13, 2007.

Non-Final Office Action mailed Sep. 6, 2013 for U.S. Appl. No. 12/002,314, filed Dec. 13, 2007.

Non-Final Office Action mailed Oct. 18, 2016 for U.S. Appl. No. 14/533,602, filed Nov. 5, 2014.

Non-Final Office Action mailed Jan. 22, 2016 for U.S. Appl. No. 14/063,956, filed Oct. 25, 2013.

Non-Final Office Action mailed May 25, 2010 for U.S. Appl. No. 12/002,314, filed Dec. 13, 2007.

Non-Final Office Action mailed Mar. 28, 2014 for U.S. Appl. No. 12/002,314, filed Dec. 13, 2007.

Polson C., et al., "Optimization of Protein Precipitation Based Upon Effectiveness of Protein Removal and Ionization Effect in Liquid Chromatography-Tandem Mass Spectrometry," Journal of Chromatography B, 2003, vol. 785 (2), pp. 263-275.

Program & Abstract, The Endocrine Society's 89Th Annual Meeting, ENDO Jun. 2-5, 2007, The Endocrine Society, 2007, pp. 1-344.

Robb D.B., et al., "Atmospheric Pressure Photoionization: An Ionization Method for Liquid Chromatography—Mass Spectrometry," Analytical Chemistry, 2000, vol. 72 (15), pp. 3653-3659.

Salm P., et al., "The Quantification of Sirolimus by High-Performance Liquid Chromatography-Tandem Mass Spectrometry and Microparticle Enzyme Immunoassay in Renal Transplant Recipients," Clinical Therapeutics, 2000, vol. 22 Suppl B, pp. B71-B85.

Seifert M., et al., "A New Concept for the Bioeffects-Related Analysis of Xenoestrogens: Hyphenation of Receptor Assays with LC-MS," Fresenius Journal of Analytical Chemistry, 1999, vol. 363 (8), pp. 767-770.

Snedden W., et al., "The Direct Determination of Oestrogen and Progesterone in Human Ovarian Tissue by Quantitative High Resolution Mass Spectrometry," Biomedical Mass Spectrometry, 1976, vol. 3 (6), pp. 295-298.

Supplementary European Search Report for Application No. EP08859581, mailed on Feb. 25, 2011, 6 pages.

Taylor P.J., et al., "Simultaneous Quantification of Tacrolimus and Sirolimus in Human Blood, by High-Performance Liquid Chromatography—Tandem Mass Spectrometry," Therapeutic Drug Monitoring, 2000, vol. 22 (5), pp. 608-612.

Wright Jr., G.L., et al., "Proteinchip Surface Enhanced Laser Desorption/Ionization (SELDI) Mass Spectrometry: A Novel Protein Biochip Technology for Detection of Prostate Cancer Biomarkers in Complex Protein Mixtures," Prostate Cancer and Prostatic Diseases, 1999, vol. 2 (5-6), pp. 264-276.

Written Opinion for Application No. PCT/US08/85282, mailed on Feb. 9, 2009, 4 Pages.

Xia Y.Q., et al., "Trace Level Quantification of Deuterated 17[beta]-estradiol and Estrone in Ovariectomized Mouse Plasma and Brain Using Liquid Chromatography/tandem Mass Spectrometry Following Dansylation Reaction," Rapid Communications in Mass Spectrometry, 2004, vol. 18 (14), pp. 1621-1628.

Xu X., et al., "A Liquid Chromatography-Mass Spectrometry Method for the Quantitative Analysis of Urinary Endogenous Estrogen Metabolites," Nature Protocols, 2007, vol. 2 (6), pp. 1350-1355.

Xu X., et al., "Measuring Fifteen Endogenous Estrogens Simultaneously In Human Urine by High-Performance Liquid Chromatography-Mass Spectrometry," Analytical Chemistry, 2005, vol. 77 (20), pp. 6646-6654.

Xu X., et al., "Quantitative Measurement of Endogenous Estrogens and Estrogen Metabolites in Human Serum by Liquid Chromatography-Tandem Mass Spectrometry," Analytical Chemistry, ACS Publications, 2007, vol. 79 (20), pp. 7813-7821.

Yamashita K., et al., "Highly Sensitive Determination of Estrone and Estradiol in Human Serum by Liquid Chromatography-Electrospray Ionization Tandem Mass Spectrometry," Steroids, 2007, vol. 72 (11-12), pp. 819-827.

* cited by examiner

Linearity – Typical Calibration Curve
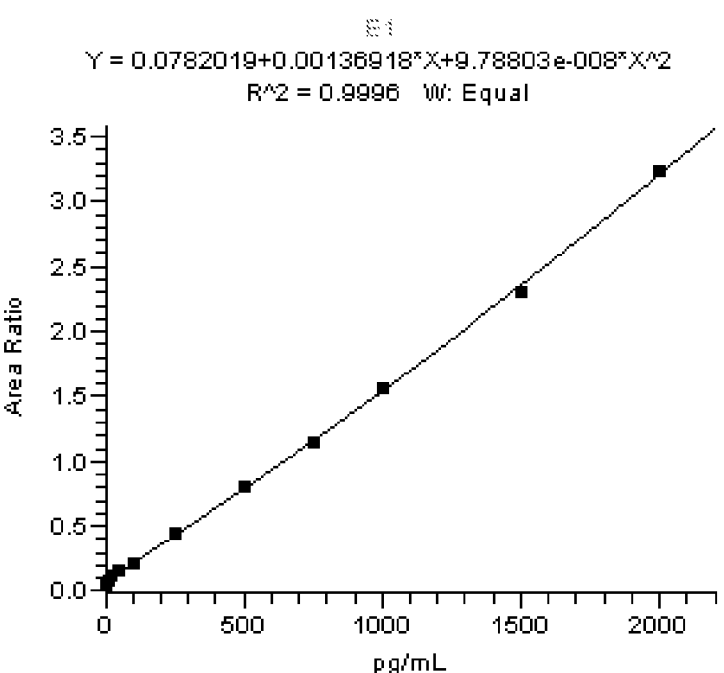

METHODS FOR DETECTING ESTRONE BY MASS SPECTROMETRY

CROSS REFERENCE TO RELATED PATENT APPLICATIONS

This application is a continuation of U.S. application Ser. No. 16/579,438, filed Sep. 23, 2019, now U.S. Pat. No. 11,280,798, which is a continuation of U.S. application Ser. No. 15/616,657, filed Jun. 7, 2017, now U.S. Pat. No. 10,422,804, which is a continuation of U.S. application Ser. No. 14/533,602, filed Nov. 5, 2014, now U.S. Pat. No. 9,678,087, which is a continuation of U.S. application Ser. No. 12/002,314, filed Dec. 23, 2014, now U.S. Pat. No. 8,916,385, each of which is incorporated by reference in its entirety herein.

FIELD OF THE INVENTION

The invention relates to the detection of estrone. In a particular aspect, the invention relates to methods for detecting estrone by mass spectrometry.

BACKGROUND OF THE INVENTION

The following description of the background of the invention is provided simply as an aid in understanding the invention and is not admitted to describe or constitute prior art to the invention.

Estrone [1,3,5 (10)-estratrien-3-ol-17-one or 3-Hydroxy-1,3,5 (10)-estratrien-17-one] or E1 is a C18 steroid hormone with a molecular weight of 270.37 daltons. Estrone is produced primarily from androstenedione originating from the gonads or the adrenal cortex. Estrone (or E1) is one of the three naturally occurring estrogens, the others being estradiol and estriol, that are natural to the human body. Its molecular formula is $C_{18}H_{22}O_2$. Estrogens are primarily responsible for the growth of female characteristics in puberty and regulating the menstrual cycle. Estrone may be measured in women who have gone through menopause to determine their estrogen levels. It may also be measured in men or women who might have cancer of the ovaries, testicles, or adrenal glands. In premenopausal women estrone levels generally parallel those of estradiol. After menopause estrone levels increase, possibly due to increased conversion of androstenedione to estrone.

Methods for detecting specific estrone ions using mass spectrometry have been described. For example Nelson R, et al., Clinical Chem 2004, 50(2):373-84, and Xu X, et al., Nature Protocols 2007, 2(6):1350-1355 disclose methods for detecting various estrone ions using liquid chromatography and mass spectrometry. These methods derivatize estrone prior to detection by mass spectrometry. Methods to detect underivatized estrone by liquid chromatography/mass spectrometry are discussed in Diaz-Cruz S, et al., J Mass Spectrom 2003, 38:917-923, and Nelson R, et al., Clinical Chem 2004, 50(2):373-84. Methods to detect estrone by gas chromatography/mass spectrometry are disclosed in Nachtigall L, et al., Menopause: J of N. Amer. Menopause Society 2000, 7(4):243-250 and Dorgan J, et al., Steroids 2002, 67:151-158.

SUMMARY OF THE INVENTION

The present invention provides methods for detecting the amount of estrone in a sample by mass spectrometry, including tandem mass spectrometry.

In one aspect, methods are provided for determining the amount of estrone in a body fluid sample. The methods may include: (a) purifying estrone in the body fluid sample by liquid chromatography; (b) ionizing estrone in the body fluid sample; and (c) detecting the amount of the estrone ion(s) by mass spectrometry and relating the amount of the detected estrone ion(s) to the amount of estrone in the body fluid sample. In certain preferred embodiments of this aspect, the limit of quantitation of the methods is less than or equal to 500 pg/mL. In other preferred embodiments, estrone is not derivatized prior to mass spectrometry. In certain preferred embodiments, estrone ions are selected from a group of ions with a mass/charge ratio of 269.07±0.5, 145.03±0.5, and 143.02±0.5. In some preferred embodiments, the methods include generating one or more precursor ions of estrone in which at least one of the precursor ions has a mass/charge ratio of 269.07±0.5. In related preferred embodiments, the methods may include generating one or more fragment ions of an estrone precursor ion in which at least one of the fragment ions has a mass/charge ratio of 145.03±0.5, or 143.02±0.5. In some preferred embodiments, the methods may include adding an agent to the body fluid sample in an amount sufficient to free estrone from a protein that may be present in the body fluid sample. In related preferred embodiments, the methods may include acidifying the body fluid sample; preferably acidifying before ionizing; more preferably acidifying before purifying; preferably acidifying with formic acid. In particularly preferred embodiments, the body fluid sample is serum, plasma, or urine.

As used herein, unless otherwise stated, the singular forms "a," "an," and "the" include plural reference. Thus, for example, a reference to "a protein" includes a plurality of protein molecules.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Samples are purified herein by various means to allow removal of one or more interfering substances, e.g., one or more substances that would interfere with the detection of selected estrone parent and daughter ions by mass spectrometry.

As used herein, the term "test sample" refers to any sample that may contain estrone. As used herein, the term "body fluid" means any fluid that can be isolated from the body of an individual. For example, "body fluid" may include blood, plasma, serum, bile, saliva, urine, tears, perspiration, and the like.

As used herein, the term "derivatizing" means reacting two molecules to form a new molecule. Derivatizing agents may include isothiocyanate groups, dinitro-fluorophenyl groups, nitrophenoxycarbonyl groups, and/or phthalalde-hyde groups, and the like.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). "Liquid chromatography" includes for example, reverse phase liquid chromatography (RPLC), high performance liquid chromatography (HPLC), and high turbulence liquid chromatography (HTLC).

As used herein, the term "high performance liquid chromatography" or "HPLC" refers to liquid chromatography in which the degree of separation is increased by forcing the mobile phase under pressure through a stationary phase, typically a densely packed column.

As used herein, the term "high turbulence liquid chromatography" or "HTLC" refers to a form of chromatography that utilizes turbulent flow of the material being assayed through the column packing as the basis for performing the separation. HTLC has been applied in the preparation of samples containing two unnamed drugs prior to analysis by mass spectrometry. See, e.g., Zimmer et al., *J. Chromatogr.* A 854: 23-35 (1999); see also, U.S. Pat. Nos. 5,968,367, 5,919,368, 5,795,469, and 5,772,874, which further explain HTLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 35 μm. As used in this context, the term "about" means±10%. In a preferred embodiment the column contains particles of about 60 μm in diameter.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means±10%. In a preferred embodiment the analytical column contains particles of about 4 μm in diameter.

As used herein, the term "on-line" or "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 2:264-76 (1999); and Merchant and Weinberger, *Electrophoresis* 21:1164-67 (2000).

As used herein, the term "operating in negative ion mode" refers to those mass spectrometry methods where negative ions are generated and detected. Similarly, the term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photoionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photoionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. Robb, D. B., Covey, T. R. and Bruins, A. P. (2000): See, e.g., Robb et al., Atmospheric pressure photoionization: An ionization method for liquid chromatography-mass spectrometry. *Anal. Chem.* 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase.

As used herein, the term "limit of quantification", "limit of quantitation" or "LOQ" refers to the point where measurements become quantitatively meaningful. The analyte response at this LOQ is identifiable, discrete and reproducible with a precision of 20% and an accuracy of 80% to 120%.

As used herein, the term "limit of detection" or "LOD" is the point at which the measured value is larger than the uncertainty associated with it. The LOD is defined arbitrarily as 2 standard deviations (SD) from the zero concentration.

As used herein, an "amount" of estrone in a body fluid sample refers generally to an absolute value reflecting the mass of estrone detectable in volume of body fluid. However, an amount also contemplates a relative amount in comparison to another estrone amount. For example, an amount of estrone in a body fluid can be an amount which is greater than a control or normal level of estrone normally present.

In a second aspect, methods are provided for determining the amount of estrone in a body fluid sample by tandem mass spectrometry that include: (a) purifying estrone in the body fluid sample by liquid chromatography; (b) generating a precursor ion of estrone having a mass/charge ratio of 269.07±0.5; (c) generating one or more fragment ions of the precursor ion in which at least one of the fragment ions has a mass/charge ratio of 143.02±0.5; and (d) detecting the amount of one or more of the ions generated in step (b) or (c) or both and relating the detected ions to the amount of estrone in the body fluid sample. In some preferred embodiments, the limit of quantitation of the methods is less than or equal to 500 pg/mL. In other preferred embodiments, estrone is not derivatized prior to mass spectrometry. In certain preferred embodiments, the methods may further include generating one or more fragment ions of an estrone precursor ion in which at least one of the fragment ions has a mass/charge ratio of 145.03±0.5. In some preferred embodiments, the methods may include adding an agent to the body fluid sample in an amount sufficient to free estrone from a protein that may be present in the body fluid sample. In related preferred embodiments, the methods may include acidifying the body fluid sample; preferably acidifying before ionizing; more preferably acidifying before purifying; preferably acidifying with formic acid. In particularly preferred embodiments, the body fluid sample is serum, plasma, or urine.

In a third aspect, methods are provided for determining the amount of estrone in a body fluid sample that include: (a) acidifying the body fluid sample with an agent in an amount sufficient to free estrone from a protein that may be present in the body fluid sample; (b) purifying estrone in the body fluid sample by liquid chromatography; (c) ionizing estrone in the body fluid sample to produce one or more ions detectable by tandem mass spectrometry; and (d) detecting the amount of the estrone ion(s) by tandem mass spectrometry in negative ion mode and relating the amount of the detected estrone ion(s) to the amount of estrone in the body fluid sample. In some preferred embodiments, the limit of quantitation of the methods is less than or equal to 500 pg/mL. In other preferred embodiments, estrone is not derivatized prior to mass spectrometry. In certain preferred embodiments, estrone ions are selected from a group of ions with a mass/charge ratio of 269.07±0.5, 145.03±0.5, and 143.02±0.5. In some preferred embodiments, the methods include generating one or more precursor ions of estrone in which at least one of the precursor ions has a mass/charge ratio of 269.07±0.5. In related preferred embodiments, the methods may include generating one or more fragment ions of an estrone precursor ion in which at least one of the fragment ions has a mass/charge ratio of 145.03±0.5 or 143.02±0.5. In some preferred embodiments, the methods may include acidifying the body fluid sample before ionizing; more preferably acidifying before purifying; preferably acidifying with formic acid. In particularly preferred embodiments, the body fluid sample is serum, plasma, or urine.

In some preferred embodiments, estrone may be derivatized prior to mass spectrometry, however, in certain preferred embodiments; sample preparation excludes the use of derivatization.

In certain preferred embodiments of the above aspects, liquid chromatography is performed using HTLC and HPLC, preferably HTLC is used in conjunction with HPLC, however other methods that can be used include for example, protein precipitation and purification in conjunction with HPLC.

Preferred embodiments utilize high performance liquid chromatography (HPLC), alone or in combination with one or more purification methods, for example HTLC or protein precipitation, to purify estrone in samples.

In certain preferred embodiments of the methods disclosed herein, mass spectrometry is performed in negative ion mode. In certain preferred embodiments, estrone is measured using APCI or ESI in negative ionization mode.

In preferred embodiments of the above aspects, both glucuronidated and non-glucuronidated estrone present in the body fluid sample are detected and measured.

In preferred embodiments, the estrone ions detectable in a mass spectrometer are selected from the group consisting of ions with a mass/charge ratio (m/z) of 269.07±0.5, 145.03±0.5, and 143.02±0.5; the latter two being fragment ions of the precursor ions. In particularly preferred embodiments, the precursor ion has a mass/charge ratio of 269.07±0.5, and the fragment ions have a mass/charge ratio of 143.02±0.5.

In preferred embodiments, a separately detectable internal estrone standard is provided in the sample, the amount of which is also determined in the sample. In these embodiments, all or a portion of both the endogenous estrone and the internal standard present in the sample is ionized to produce a plurality of ions detectable in a mass spectrometer, and one or more ions produced from each are detected by mass spectrometry.

A preferred internal estrone standard is 2,4,16,16-$d_4$ estrone. In preferred embodiments, the internal estrone standard ions detectable in a mass spectrometer are selected from the group consisting of ions with a mass/charge ratio of 273.06±0.5, 147.07±0.5, and 145.04±0.5. In particularly preferred embodiments, a precursor ion of the internal estrone standard has a mass/charge ratio of 273.06±0.5; and one or more fragment ions is selected from the group consisting of ions having a mass/charge ratio of 147.07±0.5, and 145.04±0.5.

In preferred embodiments, the presence or amount of the estrone ion is related to the presence or amount of estrone in the test sample by comparison to a reference such as 2,4,16,16-$d_4$ estrone.

In one embodiment, the methods involve the combination of liquid chromatography with mass spectrometry. In a preferred embodiment, the liquid chromatography is HPLC. A preferred embodiment utilizes HPLC alone or in combination with one or more purification methods such as for example HTLC or protein purification, to purify estrone in samples. In another preferred embodiment, the mass spectrometry is tandem mass spectrometry (MS/MS).

In certain preferred embodiments of the aspects disclosed herein, the limit of quantitation (LOQ) of estrone in test samples is less than or equal to 500 pg/mL; preferably less than or equal to 400 pg/mL; preferably less than or equal to 300 pg/mL; preferably less than or equal to 200 pg/mL; preferably less than or equal to 175 pg/mL; preferably less than or equal to 150 pg/mL; preferably less than or equal to 125 pg/mL; preferably less than or equal to 100 pg/mL; preferably less than or equal to 75 pg/mL; preferably less than or equal to 50 pg/mL; preferably less than or equal to 25 pg/mL; preferably less than or equal to 20 pg/mL; preferably less than or equal to 15 pg/mL; preferably less than or equal to 14 pg/mL; preferably less than or equal to 13 pg/mL; preferably less than or equal to 12 pg/mL; preferably less than or equal to 11 pg/mL; preferably 10 pg/mL.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.5 atomic mass unit.

The summary of the invention described above is non-limiting and other features and advantages of the invention will be apparent from the following detailed description of the invention, and from the claims.

BRIEF DESCRIPTION OF THE DRAWINGS

FIG. 1 shows the linearity of the quantitation of estrone in serially diluted stock samples using an LC-MS/MS assay. Details are described in Example 6.

DETAILED DESCRIPTION OF THE INVENTION

Methods are described for detecting and quantifying estrone in a test sample. The methods utilize liquid chromatography (LC), most preferably HTLC in conjunction with HPLC, to perform an initial purification of selected analytes, and combine this purification with unique methods of mass spectrometry (MS), thereby providing a high-throughput assay system for detecting and quantifying estrone in a test sample. The preferred embodiments are particularly well suited for application in large clinical laboratories. Estrone methods are provided that have enhanced specificity and are accomplished in less time and with less sample preparation than required in other estrone assays.

In preferred embodiments, the limit of detection (LOD) of estrone in test samples is less than or equal to 75 pg/mL; preferably less than or equal to 50 pg/mL; preferably less than or equal to 25 pg/mL; preferably less than or equal to 10 pg/mL; preferably less than or equal to 5 pg/mL; preferably less than or equal to 4.5 pg/mL; preferably less than or equal to 4 pg/mL; preferably less than or equal to 3.5 pg/mL; preferably less than or equal to 3 pg/mL; preferably less than or equal to 2.5 pg/mL; preferably 2 pg/mL.

Suitable test samples include any test sample that may contain the analyte of interest. For example, samples obtained during the manufacture of synthetic estrone may be analyzed to determine the composition and yield of the manufacturing process. In some preferred embodiments, a sample is a biological sample; that is, a sample obtained from any biological source, such as an animal, a cell culture, an organ culture, etc. In certain preferred embodiments samples are obtained from a mammalian animal, such as a dog, cat, horse, etc. Particularly preferred mammalian animals are primates, most preferably male or female humans. Particularly preferred samples include blood, plasma, serum, hair, muscle, urine, saliva, tear, cerebrospinal fluid, or other tissue sample. Such samples may be obtained, for example, from a patient; that is, a living person, male or female, presenting oneself in a clinical setting for diagnosis, prognosis, or treatment of a disease or condition. The test sample is preferably obtained from a patient, for example, blood serum.

Sample Preparation for Mass Spectrometry

Methods that may be used to enrich in estrone relative to other components in the sample (e.g. protein) include for example, filtration, centrifugation, thin layer chromatography (TLC), electrophoresis including capillary electrophoresis, affinity separations including immunoaffinity separations, extraction methods including ethyl acetate extraction and methanol extraction, and the use of chaotropic agents or any combination of the above or the like.

Various methods may be used to disrupt the interaction between estrone and protein prior to chromatography and or MS sample analysis so that the analysis can be directed to the total amount of estrone in the sample (e.g., free estrone and estrone bound to protein). Protein precipitation is one preferred method of preparing a test sample, especially a biological test sample, such as serum or plasma. Such protein purification methods are well known in the art, for example, Polson et al., *Journal of Chromatography B* 785: 263-275 (2003), describes protein precipitation techniques suitable for use in the methods. Protein precipitation may be used to remove most of the protein from the sample leaving estrone in the supernatant. The samples may be centrifuged to separate the liquid supernatant from the precipitated proteins. The resultant supernatant may then be applied to liquid chromatography and subsequent mass spectrometry analysis. In certain embodiments, the use of protein precipitation such as for example, acetonitrile protein precipitation, obviates the need for high turbulence liquid chromatography (HTLC) or other on-line extraction prior to HPLC and mass spectrometry. Accordingly in such embodiments, the method involves (1) performing a protein precipitation of the sample of interest; and (2) loading the supernatant directly onto the HPLC-mass spectrometer without using on-line extraction or high turbulence liquid chromatography (HTLC).

In other preferred embodiments, estrone may be released from a protein without having to precipitate the protein. For example, acids, salts or alcohols may be added in amounts appropriate to disrupt interaction between a protein and estrone. Exemplary such agents include formic acid, NaCl, or ethanol.

In some preferred embodiments, HTLC, alone or in combination with one or more purification methods, may be used to purify estrone prior to mass spectrometry. In such embodiments samples may be extracted using an HTLC extraction cartridge which captures the analyte, then eluted and chromatographed on a second HTLC column or onto an analytical HPLC column prior to ionization. Because the steps involved in these chromatography procedures can be linked in an automated fashion, the requirement for operator involvement during the purification of the analyte can be minimized. This feature can result in savings of time and costs, and eliminate the opportunity for operator error.

It is believed that turbulent flow, such as that provided by HTLC columns and methods, may enhance the rate of mass transfer, improving separation characteristics. HTLC columns separate components by means of high chromatographic flow rates through a packed column containing rigid particles. By employing high flow rates (e.g., 3-5 mL/min), turbulent flow occurs in the column that causes nearly complete interaction between the stationary phase and the analyte(s) of interest. An advantage of using HTLC columns is that the macromolecular build-up associated with biological fluid matrices is avoided since the high molecular weight species are not retained under the turbulent flow conditions. HTLC methods that combine multiple separations in one procedure lessen the need for lengthy sample preparation and operate at a significantly greater speed. Such methods also achieve a separation performance superior to laminar flow (HPLC) chromatography. HTLC allows for direct injection of biological samples (plasma, urine, etc.). Direct injection is difficult to achieve in traditional forms of chromatography because denatured proteins and other biological debris quickly block the separation columns. HTLC also allows for very low sample volume of less than 1 mL, preferably less than 0.5 mL, preferably less than 0.2 mL, preferably 0.1 mL.

Examples of HTLC applied to sample preparation prior to analysis by mass spectrometry have been described elsewhere. See, e.g., Zimmer et al., *J. Chromatogr.* A 854:23-35 (1999); see also, U.S. Pat. Nos. 5,968,367; 5,919,368; 5,795, 469; and 5,772,874. In certain embodiments of the method, samples are subjected to protein precipitation as described above prior to loading on the HTLC column; in alternative preferred embodiments, the samples may be loaded directly onto the HTLC without being subjected to protein precipitation. Preferably, HTLC is used in conjunction with HPLC to extract and purify estrone without the sample being subjected to protein precipitation. In related preferred embodiments, the purifying step involves (i) applying the sample to an HTLC extraction column, (ii) washing the HTLC extraction column under conditions whereby estrone is retained by the column, (iii) eluting retained estrone from the HTLC extraction column, (iv) applying the retained material to an analytical column, and (v) eluting purified estrone from the analytical column. The HTLC extraction column is preferably a large particle column. In various embodiments, one of more steps of the methods may be performed in an on-line, automated fashion. For example, in one embodiment, steps (i)-(v) are performed in an on-line, automated fashion. In another, the steps of ionization and detection are performed on-line following steps (i)-(v).

Liquid chromatography (LC) including high-performance liquid chromatography (HPLC) relies on relatively slow, laminar flow technology. Traditional HPLC analysis relies on column packings in which laminar flow of the sample through the column is the basis for separation of the analyte of interest from the sample. The skilled artisan will understand that separation in such columns is a diffusional process. HPLC has been successfully applied to the separation of compounds in biological samples but a significant amount of sample preparation is required prior to the separation and subsequent analysis with a mass spectrometer (MS), making this technique labor intensive. In addition, most HPLC systems do not utilize the mass spectrometer to its fullest potential, allowing only one HPLC system to be connected to a single MS instrument, resulting in lengthy time requirements for performing a large number of assays.

Various methods have been described for using HPLC for sample clean-up prior to mass spectrometry analysis. See, e.g., Taylor et al., *Therapeutic Drug Monitoring* 22:608-12 (2000); and Salm et al., *Clin. Therapeutics* 22 Supl. B:B71-B85 (2000).

One of skill in the art may select HPLC instruments and columns that are suitable for use with estrone. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded surface. Alkyl bonded surfaces may include C-4, C-8, C-12, or C-18 bonded alkyl groups, preferably C-18 bonded groups. The chromatographic column includes an inlet port for receiving a sample and an outlet port for discharging an effluent that includes the fractionated sample. In one embodiment, the sample (or pre-purified sample) is applied to the column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytyptic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one preferred embodiment, the HTLC may be followed by HPLC on a hydrophobic column chromatographic system In certain preferred embodiments, a TurboFlow Cyclone P® polymer-based column from Cohesive Technologies (60 µm particle, 50×1.0 mm column, 100 Å pore) is used. In related preferred embodiments, a Synergi Polar-RP®, ether-linked phenyl, analytical column from Phenomenex, Inc. (4 µm particle, 150×2.0 mm column, 80 Å pore) with hydrophilic endcapping is used. In certain preferred embodiments, HTLC and HPLC are performed using HPLC Grade Ultra Pure Water and 100% methanol as the mobile phases.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In certain preferred embodiments, estrone present in a test sample may be purified prior to ionization. In particularly preferred embodiments the chromatography is not gas chromatography. Preferably, the methods are performed without subjecting estrone, to gas chromatography prior to mass spectrometric analysis.

Detection and Quantitation by Mass Spectrometry

In various embodiments, estrone present in a test sample may be ionized by any method known to the skilled artisan. Mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

In preferred embodiments, estrone is ionized by electrospray ionization (ESI) in negative mode. In related preferred embodiments, estrone ion is in a gaseous state and the inert collision gas is argon or nitrogen. In alternative preferred embodiments, estrone is ionized by atmospheric pressure chemical ionization (APCI) in negative mode. In other preferred embodiments, estrone is ionized by electrospray ionization (ESI) or atmospheric pressure chemical ionization (APCI) in positive mode. The mass transitions of 271.17 (precursor ion) and 159.2 and 133.2 (fragment ions) can be used for detection and quantitation in positive mode.

After the sample has been ionized, the negatively or positively charged ions thereby created may be analyzed to determine a mass-to-charge ratio. Suitable analyzers for determining mass-to-charge ratios include quadrupole analyzers, ion traps analyzers, and time-of-flight analyzers. The ions may be detected using several detection modes. For example, selected ions may be detected i.e., using a selective ion monitoring mode (SIM), or alternatively, ions may be detected using a scanning mode, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion is subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

The mass spectrometer typically provides the user with an ion scan; that is, the relative abundance of each ion with a particular mass/charge over a given range (e.g., 100 to 1000 amu). The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, molecular standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of estrone. Methods of generating and using such standard curves are well known in the art and one of ordinary skill is capable of selecting an appropriate internal standard. For example, an isotope of estrone may be used as an internal standard; in certain preferred embodiments the standard is $d_4$-estrone. Numerous other methods for relating the amount of an ion to the amount of the original molecule will be well known to those of ordinary skill in the art.

One or more steps of the methods may be performed using automated machines. In certain embodiments, one or more purification steps are performed on-line, and more preferably all of the purification and mass spectrometry steps may be performed in an on-line fashion.

In certain embodiments, such as MS/MS, where precursor ions are isolated for further fragmentation, collision activation dissociation (CAD) is often used to generate the fragment ions for further detection. In CAD, precursor ions gain energy through collisions with an inert gas, and subsequently fragment by a process referred to as "unimolecular decomposition". Sufficient energy must be deposited in the precursor ion so that certain bonds within the ion can be broken due to increased vibrational energy.

In particularly preferred embodiments, estrone is detected and/or quantified using MS/MS as follows. The samples are subjected to liquid chromatography, preferably HTLC followed by HPLC, the flow of liquid solvent from the chromatographic column enters the heated nebulizer interface of an MS/MS analyzer and the solvent/analyte mixture is converted to vapor in the heated tubing of the interface. The analyte (e.g., estrone), contained in the nebulized solvent, is ionized by the corona discharge needle of the interface, which applies a large voltage to the nebulized solvent/analyte mixture. The ions, e.g. precursor ions, pass through the orifice of the instrument and enter the first quadrupole. Quadrupoles 1 and 3 (Q1 and Q3) are mass filters, allowing selection of ions (i.e., "precursor" and "fragment" ions) based on their mass to charge ratio (m/z). Quadrupole 2 (Q2) is the collision cell, where ions are fragmented. The first quadrupole of the mass spectrometer (Q1) selects precursor estrone ions with a particular mass to charge ratio. Precursor estrone ions with the correct mass/charge ratio are allowed to pass into the collision chamber (Q2), while unwanted ions with any other mass/charge ratio collide with the sides of the quadrupole and are eliminated. Precursor ions entering Q2 collide with neutral argon gas molecules and fragment. This process is called collision activated dissociation (CAD). The fragment ions generated are passed into quadrupole 3 (Q3), where the fragment ions of estrone are selected while other ions are eliminated.

The methods may involve MS/MS performed in negative or positive ion mode. Using standard methods well known in the art, one of ordinary skill is capable of identifying one or more fragment ions of a particular precursor ion of estrone that may be used for selection in quadrupole 3 (Q3).

If the precursor ion of estrone includes an alcohol or amine group, fragment ions are commonly formed that represent dehydration or deamination of the precursor ion, respectfully. In the case of precursor ions that include an alcohol group, such fragment ions formed by dehydration are caused by a loss of one or more water molecules from the precursor ion (i.e., where the difference in mass to charge ratio between the precursor ion and fragment ion is about 18 for the loss of one water molecule, or about 36 for the loss of two water molecules, etc.). In the case of precursor ions that include an amine group, such fragment ions formed by deamination are caused by a loss of one or more ammonia molecules (i.e. where the difference in mass to charge ratio between the precursor ion and fragment ion is about 17 for the loss of one ammonia molecule, or about 34 for the loss of two ammonia molecules, etc.). Likewise, precursor ions that include one or more alcohol and amine groups commonly form fragment ions that represent the loss of one or more water molecules and/or one or more ammonia molecules (i.e., where the difference in mass to charge ratio between the precursor ion and fragment ion is about 35 for the loss of one water molecule and the loss of one ammonia molecule). Generally, the fragment ions that represent dehydrations or deaminations of the precursor ion are not specific fragment ions for a particular analyte. Accordingly, in preferred embodiments of the invention, MS/MS is performed such that at least one fragment ion of estrone is detected that does not represent only a loss of one or more water molecules and/or a loss of one or more ammonia molecules from the precursor ion.

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC methods. The areas under the peaks corresponding to particular ions, or the amplitude of such peaks, are measured and the area or amplitude is correlated to the amount of the analyte (estrone) of interest. In certain embodiments, the area under the curves, or amplitude of the peaks, for fragment ion(s) and/or precursor ions are measured to determine the amount of estrone. As described above, the relative abundance of a given ion may be converted into an absolute amount of the original analyte, e.g., estrone, using calibration standard curves based on peaks of one or more ions of an internal molecular standard, such as $d_4$-estrone.

The following examples serve to illustrate the invention. These examples are in no way intended to limit the scope of the methods.

EXAMPLES

Example 1: Sample and Reagent Preparation

Blood was collected in a Vacutainer with no additives and allowed to clot 30 minutes at room temperature, 18° to 25° C. Samples that exhibited gross hemolysis, lipemia, and/or icteria were excluded.

An estrone stock standard of 1 mg/mL in methanol was prepared and further diluted in methanol to prepare an estrone intermediate stock standard of 1,000,000 pg/mL, which was used to prepare two estrone working standards of 10,000 pg/mL, diluted in either methanol for standard A or in stripped serum for standard B.

Deuterated methanol (methyl-$d_1$ alcohol; Fisher Cat. No. AC29913-1000 or equivalent) was used to prepare a 1 mg/mL $d_4$-estrone stock standard (2,4,16,16-$d_4$ estrone), which was used to prepare a 1,000,000 pg/mL intermediate stock standard in deuterated methanol. The $d_4$-estrone intermediate stock standard was used to prepare a working $d_4$-estrone internal standard of 5000 pg/mL in DI water: 1 mL of the $d_4$-estrone intermediate stock standard was diluted to volume with DI water in a 200 mL volumetric flask.

A 20% formic acid solution was prepared by adding 50 mL of formic acid (~98% pure Aldrich Cat. No. 06440 or equivalent) to a 250 mL volumetric flask, which was diluted to volume with ultrapure HPLC-grade water.

All calibrators/standards used in each run were prepared fresh weekly from series of dilutions of frozen aliquots of 10,000 pg/mL estrone standard in stripped serum. The standards were prepared from highest concentration to the lowest with a final total volume for each standard of 10 mL.

Example 2: Extraction of Estrone from Serum Using Liquid Chromatography

Liquid chromatography (LC) samples were prepared by pipetting 200 μL of standards, controls, or patient samples into a 96-well plate. In addition, 300 μL of 20% formic acid were delivered to each well for a final concentration of ~11% (V/V). Finally, 50 μL of the 5000 pg/mL $d_4$-estrone standard were added to each well. The samples were incubated at room temperature for 30 minutes prior to LC.

Liquid chromatography was performed with a Cohesive Technologies Aria TX-4 HTLC system using Aria OS V 1.5 or newer software. An autosampler wash solution was prepared using 60% acetonitrile, 30% isopropanol, and 10% acetone (V/V).

The HTLC system automatically injected 75 μL of the above prepared samples into a TurboFlow column (50×1.0 mm, 60 μm Cyclone P Extraction Column from Cohesive Technologies) packed with large particles. The samples were loaded at a high flow rate (5 mL/min, loading reagent 100% DI water) to create turbulence inside the extraction column. This turbulence ensured optimized binding of estrone to the large particles in the column and the passage of residual protein and debris to waste.

Following loading, the flow direction was reversed and the sample eluted off to the analytical column (Phenomenex analytical column, Synergi Polar-RP® 150×2.0 mm, 4 μm column) with 200 μL of 90% methanol in the loop. A binary HPLC gradient was applied to the analytical column, to separate estrone from other analytes contained in the sample.

Mobile phase A was Ultra Pure Water (HPLC grade) and mobile phase B was 100% methanol. The HPLC gradient started with a 10% organic gradient that ramped up to 75% and then increased in 5 to 10% increments up to 99% in approximately 3.35 minutes. The total gradient time was 6.58 minutes. The separated sample was then subjected to MS/MS for quantitation of estrone.

To determine interference with other molecules, blank sera was spiked with 1000 pg/mL of the following steroids: 17-β Estradiol, Estriol, Testosterone, 17-α Hydroxyprogesterone, Progesterone, Androstenedione, Aldosterone, 11-Deoxycortisol, Corticosterone and Dihydroxytestosterone. The samples were subject to LC. There was no interference observed from these steroids; none of the steroids co-eluted with estrone.

Example 3: Detection and Quantitation of Estrone by MS/MS

MS/MS was performed using a Finnigan TSQ Quantum Ultra MS/MS system (Thermo Electron Corporation). The following software programs all from ThermoElectron were used in the Examples described herein: Tune Master V 1.2 or newer, Excalibur V 2.0 SR1 or newer, TSQ Quantum 1.4 or newer, LCQuan V 2.5 SUR1 or newer, and XReport 1.0 or newer. Liquid solvent/analyte exiting the analytical HPLC column flowed to the heated nebulizer interface of a Thermo Finnigan MS/MS analyzer. The solvent/analyte mixture was converted to vapor in the heated tubing of the interface. Analytes in the nebulized solvent were ionized by the corona discharge needle of the interface, which applied voltage to the nebulized solvent/analyte mixture.

Ions passed to the first quadrupole (Q1), which selected ions with a mass to charge ratio of 269.07±0.5 m/z. Ions entering Quadrupole 2 (Q2) collided with argon gas to generate ion fragments, which were passed to quadrupole 3 (Q3) for further selection. Simultaneously, the same process using isotope dilution mass spectrometry was carried out with an internal standard, a 4-deuterated estrone molecule. The following mass transitions were used for detection and quantitation during validation on negative polarity.

TABLE 1

| Mass Transitions for Estrone (Negative Polarity) | | |
| --- | --- | --- |
| Analyte | Precursor Ion (m/z) | Product Ion (m/z) |
| Estrone | 269.07 | 143.02 & 145.03 |
| 2,4,16,16-$d_4$ Estrone | 273.06 | 145.04 & 147.07 |

The following mass transitions were used for detection and quantitation during validation on positive polarity.

TABLE 2

| Mass Transitions for Estrone (Positive Polarity) | | |
| --- | --- | --- |
| Analyte | Precursor Ion (m/z) | Product Ion (m/z) |
| Estrone | 271.17 | 159.20 & 133.20 |
| 2,4,16,16-$d_4$ Estrone | 275.12 | 159.10 |

Example 4: Intra-Assay and Inter-Assay Precision and Accuracy

Three quality control (QC) pools were prepared from charcoal stripped serum, spiked with estrone to a concentration of 25, 200, and 800 pg/mL.

Ten aliquots from each of the three QC pools were analyzed in a single assay to determine the reproducibility (CV) of a sample within an assay. The following values were determined:

TABLE 3

| Intra-Assay Variation and Accuracy | | | |
| --- | --- | --- | --- |
| | Level I (25 pg/mL) | Level II (200 pg/mL) | Level III (800 pg/mL) |
| Mean | 25 | 213 | 845 |
| Stdev | 0.7 | 22.4 | 77.4 |
| CV | 3% | 10% | 9% |
| Accuracy | 98% | 107% | 106% |

Ten aliquots from each of the three QC pools were assayed over 5 days to determine the reproducibility (RSD %) between assays. The following values were determined:

TABLE 4

| Inter-Assay Variation and Accuracy | | | |
| --- | --- | --- | --- |
| | Level 1 (25 pg/mL) | Level II (200 pg/mL) | Level III (800 pg/mL |
| Mean | 26 | 224 | 882 |
| Stdev | 2.5 | 20.6 | 71.2 |
| RSD (%) | 6.9 | 8.2 | 7.8 |
| Accuracy (%) | 104.0 | 112.2 | 110.2 |

Example 5: Analytical Sensitivity: Limit of Detection (LOD) and Limit of Quantitation (LOQ)

The estrone zero standard was run in 10 replicates to determine the limit of detection of the assay, which is the point at which the measured value is larger than the uncertainty associated with it. The LOD was defined arbitrarily as 2 standard deviations (SD) from the zero concentration. The resulting peak area ratios for the zero standard were statistically analyzed with a mean value of 0.014 and a SD of 0.004. The LOD for the estrone assay was 2.0 pg/mL.

To determine the limit of quantitation with a precision of 20% and an accuracy of 80% to 120%, five different samples at concentrations close to the expected LOQ were assayed and the reproducibility determined for each. The LOQ for the estrone assay was defined at 10.0 pg/mL.

Example 6: Assay Reportable Range and Linearity

To establish the linearity of estrone detection in the assay, one blank assigned as zero standard and 10 spiked serum standards were prepared and analyzed on 5 separate days. A quadratic regression from five consecutive runs yielded coefficient correlations of 0.995 or greater, with an accuracy of ±20% revealing a quantifiable linear range of 10 to 2000 pg/mL.

Example 7: Matrix Specificity

Matrix specificity was evaluated using water, stripped serum, and Biocell normal human serum to determine whether patient samples could be diluted in a linear fashion. The mid (MC) and high controls (HC) were diluted two-fold and four-fold. The samples were run in duplicate following a calibration run. The accuracy was as follows:

TABLE 5

| Matrix Specificity Accuracy | | | |
| --- | --- | --- | --- |
| | Water Recovery % MC/HC | Stripped Serum Recovery % MC/HC | Pooled Serum Recovery % MC/HC |
| 1:2 Dilution | 121/89 | 84/110 | 84/97 |
| 1:4 Dilution | 164/116 | 113/92 | 25/90 |

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

We claim:

1. A method for determining an amount of estrone in a human serum or plasma sample, the method comprising:

(a) adding deuterated estrone to a human serum or plasma sample;

(b) purifying the estrone and the deuterated estrone from the human serum or plasma sample by high performance liquid chromatography (HPLC);

(c) ionizing the purified estrone and deuterated estrone to produce one or more of estrone ions and deuterated estrone ions detectable by mass spectrometry, wherein the deuterated estrone ions comprise an ion having a mass/charge ratio of 159.10±0.5; and (d) detecting the amount of the estrone ions by tandem mass spectrometry, wherein the amount of the estrone ions is correlated to the amount of estrone in the human serum or plasma sample.

2. The method of claim 1, wherein the deuterated estrone is $d_4$-estrone.

3. The method of claim 1, wherein the deuterated estrone is 2,4,16,16-$d_4$ estrone.

4. The method of claim 1, wherein the method further comprises subjecting estrone from the human serum or plasma sample to an additional extraction.

5. The method of claim 1, wherein the method has a limit of quantitation less than or equal to 20 pg/mL.

6. The method of claim 1, wherein the method has a limit of detection less than or equal to 10 pg/mL.

7. The method of claim 1, wherein the ionization is atmospheric pressure chemical ionization (APCI) or electrospray ionization (ESI).

8. The method of claim 1, wherein the ionization is in a positive ion mode or a negative ion mode.

* * * * *